(12) United States Patent
Purcell

(10) Patent No.: US 6,559,182 B1
(45) Date of Patent: May 6, 2003

(54) METHOD FOR TREATMENT OF ENVELOPED VIRUSES USING JOJOBA OIL ESTERS

(75) Inventor: Hal Purcell, Avila Beach, CA (US)

(73) Assignee: Purcell Jojoba International, LLC, Avila Beach, CA (US)

( * ) Notice: Subject to any disclaimer, the term of this patent is extended or adjusted under 35 U.S.C. 154(b) by 0 days.

(21) Appl. No.: 10/039,360

(22) Filed: Nov. 7, 2001

(51) Int. Cl.⁷ .................. A61K 35/78; A61K 31/23
(52) U.S. Cl. .................. 514/552; 427/725
(58) Field of Search .................. 424/195.1, 125; 514/552

(56) References Cited

U.S. PATENT DOCUMENTS

| | | | |
|---|---|---|---|
| 4,585,656 A | * | 4/1986 | Rosenthal et al. ....... 424/195.1 |
| 5,190,977 A | * | 3/1993 | Herman .................. 514/724 |
| 5,229,130 A | * | 7/1993 | Sharma et al. ........... 424/449 |
| 5,238,933 A | * | 8/1993 | Catz et al. .............. 514/236.2 |
| 5,534,554 A | * | 7/1996 | Katz et al. .............. 514/724 |
| 5,650,157 A | * | 7/1997 | Bockow ................. 424/104 |
| 5,750,563 A | * | 5/1998 | Honda .................. 514/460 |
| 5,945,409 A | * | 8/1999 | Crandall ................. 514/78 |
| 5,952,392 A | * | 9/1999 | Katrz et al. ............. 514/724 |
| 6,251,878 B1 | * | 6/2001 | Strickland et al. ......... 514/54 |
| 6,361,806 B1 | * | 3/2002 | Allen ................... 424/740 |
| 2001/0012840 A1 | * | 8/2001 | Verbiscar ............... 514/164 |

* cited by examiner

Primary Examiner—James H Reamer
(74) Attorney, Agent, or Firm—Fitch, Even, Tabin & Flannery

(57) ABSTRACT

The present invention is directed to the use of jojoba oil esters to treat and prevent envelope virus infections. Jojoba oil esters applied to the skin alone or in combination with other compounds are effective for treating and preventing viral infections.

21 Claims, No Drawings

METHOD FOR TREATMENT OF ENVELOPED VIRUSES USING JOJOBA OIL ESTERS

The present invention relates to a method for treating and preventing infections caused by enveloped viruses. More particularly, jojoba oil esters are used to treat and prevent envelope virus infections.

BACKGROUND

Enveloped virus infections occur in a very large segment of the population and are one of the commonest infections of mankind throughout the world. The class of enveloped virus includes herpes virus, e.g., herpes simplex 1 and 2; myxovirus, e.g., influenza virus; paramyxovirus, e.g., virus responsible for measles and mumps, and respiratory syncitial virus responsible for croup; corona virus, which is also implicated in the common cold; and toga virus, e.g., rubella virus and virus responsible for encephalitis and hemorrhagic fever, Varicella Zoster Virus, Human Herpesvirus-6, cytomegaolovirus, and HIV-1.

There are two main types of herpes simplex virus (HSV). HSV1 is mainly associated with lip, mouth, nose and eye facial infections and HSV2 is mainly genital. Both type 1 and type 2 herpes simplex viruses reside in a clinically latent state in the ganglion of sensory nerves going from the skin toward the central nervous system. With each attack of herpes simplex the virus grows down the nerves and out into the skin or mucous membranes where it multiplies, causing a clinical lesion. After each attack it travels back up the nerve fiber to the ganglion. Herpes simplex, a permanent resident in the nerve tissue of infected humans, causes recurrent acute outbreaks in the skin that are self-limiting and cause pain and embarrassment due to the unsightly redness, swelling and ulceration around the prominently visible lips and nose. When the central part of the cornea of the eye is infected (herpes keratitis) scarring and loss of vision can result if the infection penetrates through the epithelium into the corneal stromal tissue.

HSV can be shed and spread to others in the saliva and genital secretions from individuals without symptoms, especially in the days and weeks following a clinical attack. Following the initial infection, immunity develops but it does not fully protect against further attacks. However where immunity is deficient, both initial and recurrent infections tend to occur more frequently and are more pronounced.

Recurrences of HSV infections can be triggered by minor trauma, other infections including minor upper respiratory tract infections, colds, fevers, chapped lips, ultraviolet radiation (sunlight or artificial tanning devices), conditions affecting the nerves of the face, operations on the face nerves, dental surgery, dermabrasion or laser resurfacing, menstrual cycle (flare-ups may occur before the monthly period), emotional stress and general fatigue, and in many cases no reason for the eruption is evident. Recurrent infections differ from first infections in the smaller size of the vesicles and their close grouping. Recurrent attacks do not usually affect the inside of the mouth. Generally the affected person feels quite well. Tingling, itching or burning precedes by minutes up to a few hours the development of small, closely grouped vesicles in an inflamed area. They normally heal in 7–10 days without scarring. They occur most frequently around the mouth and nose, but can be situated anywhere on the body, particularly where dry skin meets mucosa (wet skin). Recurrences tend to be in the same region, but are not always at the identical site. The vesicles often form in repeated irregular clusters. Fever, pain and enlarged lymph nodes may also be associated with herpes of the hand and forearm or other areas.

As to genital herpes, recurrences are fairly common with clusters of small vesicles which produce shallow ulcers on the glans or shaft of the penis. Similar lesions may occur on the labia, vagina or cervix and can cause distressingly painful symptoms. In other individuals the lesions can be unnoticed.

Stages of recurrent Herpes simplex infection can be summarized as follows: (1) prodromal (tingling, buring and itching.), 99.5% of patients experience this (J. Der. Aug. 2001); (2) papule (redness and slight elevation); (3) vesicle (blister or usually a series of blisters); (4) ulcer/soft crust (loss of skin with soft grey crust); (5) hard crust (dark red scab formation); and (6) healing (diminishing redness until completely healed).

Viral infections have in the past been largely resistant to antibiotic therapy. In particular, herpes infections have proven to be especially refractory. Recent research has shown that certain lipophilic compounds inhibit replication of some enveloped viruses in vitro (U.S. Pat. No. 5,534,554). Sands (Antimicrobial Agents and Chemotherapy, 12, 523–528 (1977)), describes various fatty acids that can inhibit viral replication in bacteriophage, and that at least two modes of fatty acid inhibition can be involved. The first mode involves inactivation of the virus, i.e., virucidal activity. Oleic acid, a monounsaturated C18 fatty acid, was the most effective fatty acid tested for this property, but a C18 acid having two double bonds was essentially inactive. The second method is inhibition of replication, without killing the virus, i.e., anti-viral or virustatic activity. This phenomenon is related to the stage in the infectious cycle in which the fatty acid is added.

Reinhardt et al. (J. Virology, 25, 479–485 (1978)), described unsaturated fatty acids that can inhibit the viral replication of PR4 bacteriophage in vitro. The most effective acids were oleic acid and palmitoleic acid. Arachidonic acid (C20 tetraene) was moderately effective, but less effective than linolenic acid (C18 triene).

Sands et al. (Antimicrobial Agents and Chemotherapy, 15, 67–73 (1979)) describes antiviral activity in vitro of C14–20 unsaturated alcohols having 1–4 double bonds, the most active being gamma-linolenyl alcohol (6,9,12-octadecatrien-1-ol), while C20 tetraenyl alcohol had the least activity. Lower antiviral activity in vitro was described for saturated alcohols by Snipes et al. (Ibid., 11, 98–104 (1977), and Snipes et al. (Symp. Pharm. Effects Lipids (AOCS Monograph No. 5), 63–74 (1978)). Further, U.S. Pat. No. 5,534,554 describes the use of creams containing 20 to 28 carbon aliphatic alcohols for the treatment of viral and inflammatory disease.

In practice, the clinical treatment of enveloped virus infection may include a number of different treatment options. For example, the use of high SPF sunscreens and stress management are important to prevent recurrent facial herpes simplex. Further, herpes simplex infections have been treated using treatments such as ABREVA OTC with 10% docosanol as the active ingredient and with antiviral drugs that include acyclovir, valacyclovir, famciclovir. These drugs will stop the herpes simplex virus from multiplying once it reaches the skin or mucous membranes but cannot eradicate the virus from its resting stage within the nerve cells. They can therefore shorten and prevent attacks while the drug is being taken, but a single course cannot prevent future attacks.

Topical acyclovir, in the form of a cream, can shorten an attack of recurrent herpes simplex, provided it is started early enough. Antiviral drugs are indicated for severe frequently recurring herpes simplex infections. Patients with significant recurring herpes simplex, particularly of the genital type, may require repeated courses or continuous prophylactic therapy for several months or more at a time.

One deficiency with docosanol, which is a saturated solid material containing particles averaging 0.1 microns in size, and with acyclovir for treatment of viral infections, is that they have limited ability to be adsorbed into the skin. It is necessary to add surfactants and emollients to improve penetration (U.S. Pat. No. 5,534,554). Because n-Docosanol is a solid, it was a challenge to add the optimal proportions of emollients and surfactants to attain adequate percutaneous adsorption. The same was true for other long chain compounds tested (PCT W098/11887; U.S. Pat. No. 5,952,392; Parry et al., J. Invest. Dermatol., 98(6): 856–863 (1992); Spruance et al., Antimicrob. Agents Chemother., 25(1): 10–15 (1984)). Topical treatments to the skin or mucosa for genital herpes infections have the same deficiency.

Topical treatments may also have the potential to act as adjuvants. Dendritic cells are one of the most potent antigen-presenting cells identified to date, and may be the only cells that can activate naive (previously unstimulated) T cells in a primary immune response (Banchereau and Steinman, (1998) Nature 392: 245–252). activation of naive T cells is necessary if a vaccine is to produce full T cell (immunity and optimal antibody responses. Dendritic cells have this capacity due to their expression of high levels of the ligands required to activate naive T cells—namely, MHC:peptide complexes, co-stimulatory molecules and intercellular adhesion molecule (Sprent, (1999) J Immunol. 163: 4629–4636).

One problem in vaccine development is that dendritic cells are rare. They comprise approximately $1/400$ cells in secondary lymphoid organs, $1/500$ white blood cells and $<1/1000$ cells in most non-lymphoid organs. Their scarcity is compounded by the low frequency of naive T-cells able to respond to any single antigenic epitope, or MHC:peptide complex, estimated to be $1/10.\text{sup}.5$ to $1/10^4$ (Mason, 1998) Immunol. Today 19: 395–404). Hence, induction of an immune response depends upon antigen reaching one rare cell, that must then interact with another rare cell, which would seem to militate against the development of immunity.

Naive T cells continuously recirculate through lymph nodes via the bloodstream (Gretz et al. (1996) J Immunol. 157: 495–499), whereas immature dendritic cells are relatively stable residents of non-lymphoid organs (Cowing and Gilmore, (1992) J. Immunol. 148: 1072–1079). Immature dendritic cells express low levels of surface MHC and co-stimulatory molecules and, as such, are only weak stimulators of T cell activation. However, these cells are actively pinocytic and phagocytic, enabling them to sample their environment for the presence of potential pathogens. When exposed to appropriate stimuli, immature dendritic cells are mobilized. Local tissue-specific adhesion molecules are down-regulated, permitting the cells to disengage from the tissue and migrate via afferent lymphatics to draining lymph nodes (Banhereau and Steinman, (1998) Nature 392: 245–252).

During their migration to lymph nodes, immature dendritic cells undergo "maturation" to become potent inducers of T cell activation. Maturation is characterized by 1) down-regulation of pinocytosis and phagocytosis, and 2) increased surface expression of MHC molecules that are loaded with peptides newly derived from proteins recently taken up from the environment. The expression of co-stimulatory molecules and intercellular adhesion molecules is up-regulated during maturation, while the pattern of chemokine receptor expression is altered, enabling the migrating dendritic cells to follow the correct route to the paracortical, T cell-rich areas of the draining lymph node (Banchereau and Steinman, (1998) Nature 392: 245–252). Once induced to migrate from their tissue of residence to the regional lymph node, mature antigen-bearing dendritic cells will be positioned to be encountered by antigen-specific naive T cells present in the recirculating pool of lymphocytes.

Langerhans cells are perhaps the best studied of the immature dendritic cells and serve as a prototype of immature dendritic cells in non-lymphoid organs. They reside in the epidermal layer of the skin and mucous membranes, where they are present in higher frequency (i.e., 1 to 2%) than the immature dendritic cells found in other non-lymphoid organs. Langerhans cells are bound to neighboring keratinocytes via the homophillic adhesion molecule E-cadherin (Udey, (1997) Clin. Exp. Immunol. 107 (Suppl. 1): 6–8). This bond must be attenuated before the Langerhans cell can become mobile. Signals known to mobilize immature dendritic cells (e.g., IL-1, TNF-alpha., and LPS) have also been shown to decrease the expression of E-cadherin on Langerhans cell-like dendritic cells, induing the loss of E-cadherin-mediated adhesion (Jakob and Udey 1998 J. Immunol. 160: 4067–4073). Once released from surrounding keratinocytes, Langerhans cells pass through the basement membrane of the epidermis into the dermis, enter afferent dermal lymphatics and migrate to skin-draining lymph nodes. As detailed above, during this migration, Langerhans cells mature to acquire very high levels of surface MHC, co-stimulatory and adhesion molecules, and begin to express chemokines that attract naive T cells (Banchereau and Steinman, (1998) Nature 392: 245–252) Once in the draining lymph node, Langerhans cells remain there for a few days and then disappear (Ruedl et al. (2000) J. Immunol. 165: 4910–4916).

Whether mature antigen-bearing dendritic cells will be encountered by and activate naive T cells in the lymph node is likely to depend on three factors: 1) the number of antigen-bearing dendritic cells that enter the node, (2) the density of MHC:peptide complexes expressed on their membranes, and 3) the frequency of antigen-specific T cells in the recirculating pool. Activation of naive T cells is a stochastic process, and the magnitude of the response increases with increasing density of MHC:peptide complexes on the antigen-presenting cell (Reay et al. (2000) J. Immunol. 164: 5626–5634; Wherry et al. (1999) J. Immunol. 163: 3735–3745). Similarly, the initial encounter between a dendritic cell and a naive antigen-specific T cell is most likely stochastic and should increase with increasing frequency of either cell type. For example, an administration of antigen that resulted in no detectable interaction between antigen-bearing dendritic cells and antigen-specific T cells in normal mice, was found to be immunogenic in mice that had an artificially high frequency of antigen-specific T cells (approximately $1/10.\text{sup}.3$) due to the transfer of T cells containing an antigen-specific T cell receptor transgene (Manickasingham and Reise Souse, (2000) J. Immunol. 165: 5027–5034). Based on the preceding considerations, a critical component of vaccine immunogenicity is the capture of vaccine antigens by rare, immature dendritic cells and the induction of their maturation and migration to draining lymph nodes, in numbers sufficient to be encountered by rare, antigen-specific T cells.

The induction of dendritic cell migration is a complex process that is incompletely understood at present, but certain signals have the capacity to mobilize or induce the migration of immature dendritic cells from their tissue of residence. They include the pro-inflammatory cytokines, TNF-alpha. and IL-1, and bacterial lipopolysaccharide (LPS) (Kimber et al. (2000) Brit. J. Derm. 142: 401–412). These signals, along with GM-CSF and other cytokines, initiate the maturation process as well. Physical trauma to a tissue, such as surgical excision, also may induce the migration and maturation of resident immature dendritic cells (Steinman et al. (1995) J. Invest. Dermatol. 105: 2S–7S).

The paucity and functional immaturity of dendritic cells in non-lymphoid organs may explain why injection of an aqueous solution of most protein or peptide antigens results in little or no immunity and can even result in immunologic tolerance (Davila and Celis, (2000) J. Immunol. 165: 539–547; Garza et al. (2000) J. Exp. Med. 191: 2021–2027; Liblau et al. (1997) Immunol. Today 18: 599; Weiner, (1997) Immunol. Today 18: 335). Only a few dendritic cells are likely to be exposed to the antigen; and, in the absence of a stimulus for dendritic cell migration and maturation, those cells may never reach regional lymph nodes for recognition by recirculating T cells. Conversely, if the antigen is presented by cells that lack co-stimulatory and adhesion molecules, antigen-specific T cell tolerance can ensue. Genetic vaccines, comprising DNA or RNA encoding the antigen(s), also require processing of the protein product by host dendritic cells (Iwasaki et al. (1997) J. Immunol. 159: 11) and thus are subject to the same constraints.

In summary, there is a need for an effective method to a) promote the capture of vaccine antigens by rare, immature dendritic cells, and b) induce the maturation of antigen-loaded dendritic cells and their migration to draining lymph nodes, in numbers sufficient to be encountered by rare, antigen-specific T cells. Such a method would function as an adjuvant to generate an adaptive immune response to an otherwise weak or non-immunogenic administration of antigen.

SUMMARY

The present invention is directed to methods for treating and preventing infections caused by enveloped viruses. In accordance with the method of the invention, the situs of the virus or the virus itself is contacted with an virustatically effective amount of jojoba oil esters. The mixture of esters present in the jojoba oil are effective for inhibiting replication of a variety of enveloped viruses. The jojoba oil esters are effective for promoting a rapid healing of the infected area and/or prevention of further outbreaks. Jojoba oil esters of the present invention contain a high percentage of multiple potentially active esters as opposed to a low percentage of a limited number of active components (i.e., docosanol). Jojoba absorbs into the skin much easier and faster than the prior products without the necessity of adding surfactants and emollients. Minutes are of the essence in treatment of viral diseases such as herpes simplex. Hence, the greater variety of jojoba oil esters present and their resulting metabolites have a better chance of reaching the target and interfering with viral replication than would a single active ingredient.

The jojoba oil esters of the present invention are a mixture of esters. The esters are long chain, linear cis-monounsaturated liquid aliphatic esters of the fatty acids and fatty alcohols. The fatty acids that are esterified with the fatty alcohols include from about 4.0% to about 8.0% C18:1 fatty acid, from about 35% to about 40% C20:1 fatty acid, from about 6% to about 8.5% C22:1 fatty acid, and from about 0.5% to about 1.5% C24:1 fatty acid. The fatty alcohols that are esterified with the fatty acids include from about 0.5% to about 1.0% C18:1 fatty alcohol, from about 19% to about 26.5% C20:1 fatty alcohol, from about 18% to about 23.5% C22:1 fatty alcohol, and from about 2% to about 5% C24:1 fatty alcohol. In this aspect of the invention, the esterified fatty alcohols and fatty acids are about 95 to about 99.5% of the jojoba oil ester preparation, and in a preferred aspect of the invention from about 97.2 to about 99.1% of the jojoba oil ester preparation.

In an important aspect of the invention, the jojoba oil esters are liquid at ambient temperatures down to about 7° C. and have a viscosity of about 33 cp to about 37 cp at 25° C. The liquid nature of the jojoba oil esters provides them with superior spreadability such that they are easy to apply and are not irritating to skin, mucosa or eyes, and feel good on the skin of patients. The jojoba oil esters are rapidly absorbed into the epidermal portion of the skin for rapid onset of action and are released slowly so as to be effective about 6–8 hours. In this aspect of the invention, the jojoba oil esters absorb into the skin within about 30 to about 70 minutes and more than about 50% of the jojoba oil esters are absorbed into the skin in about 20 to about 40 minutes. The jojoba oil esters are not phototoxic or photoallergenic and have low toxicity, for example an $LD_{50}$ of more than about 160 g/Kg.

The jojoba oil esters of the present invention are resistance to oxidation by sunlight and thermal oxidation, and as a result, retain their effectiveness over a long period of time. In this aspect of the invention, the jojoba oil esters have an oxidative stability of at least about 68 hours at 110° C. and a thermal stability of at least about 265° C.

In another important aspect, the present invention provides a method of treating lesions associated with a herpes infection in an animal or human subject which involves applying jojoba oil esters to an inflamed area in an amount effective for reducing or arresting the lesions. In this aspect of the invention, from about 0.5 grams to about 1.0 grams jojoba oil esters having a purity of at least about 98% are applied to an infected area.

The virustatic properties of the jojoba oil esters of the present invention are useful to prevent the spread of enveloped virus through direct application of jojoba oil esters or through application of compositions that contain jojoba oil esters. Examples of such compositions include hand cream or lotion and fluids used to kill viruses on instruments. The safety of the jojoba oil esters further enhances their attractiveness for prophylactic use.

In another aspect of the invention, jojoba oil esters may be used to enhance the therapeutic effectiveness of other active ingredients. Jojoba oil esters of the present invention enhance percutaneous adsorption and epidermal storage and may act as a carrier vehicle to transport other active ingredients into the optimal depth of the skin for their function. Examples of active ingredients whose efficacy can be enhanced include immune response modulators such as imiquimod, anti-inflammatory drugs such as ibuprofen and ketoprofen, antifungal agents such as griseofulvin and Lamisil, lipophilic vitamins such as vitamin A (β-cartoene, retinol), vitamin D (cholecalciferol), and vitamin E (tocopherols), anti-neoplastic agents such as Taxol and Pacitaxel, hormonal agents such as testosterone, estrogen, cortisones and prostaglandins, hair growth stimulators such as minoxidyl, as well as other anti-viral agents such as nucleoside analogue drugs and immune response modifiers. Mixing of the active ingredients with the jojoba oil esters of the present invention and application of the mixture to the skin is effective for enhancing the effectiveness of these active ingredients as compared to the effectiveness of the same amount of active agent applied to the skin without jojoba oil esters.

In another aspect, the present invention also provides a method for modulating an immune response. Another approach to anti-viral therapy, including HSV, includes the use of immune response modifiers such as imiquimod. The lipophilic jojoba oil ester molecules penetrate the stratum corneum into the deeper stratum spinosum where the rare, but immunologically important, Langerhans dendritic cells are found. The jojoba oil esters of the present invention are effective for carrying immune response modulators to these cells and thereby increasing the dose of active agent delivered, the duration of exposure to the agent, and/or the ability of the active agent to enhance the migration of epidermal Langerhans cells to draining lymph nodes as compared to immune response modifier applied without jojoba oil esters. In this aspect of the invention, the jojoba oil esters may also act as adjuvants to enhance the immune response to a given antigen.

DETAILED DESCRIPTION

The jojoba oil esters of the present invention are effective as virustatic agents for a number of enveloped viruses. In addition to their virustatic properties, the jojoba oil ester preparations of the present invention are effective for relieving pain and inhibiting virus replication to prevent visible outbreak signs of redness, swelling, ulceration and bleeding.

Jojoba Oil Esters

Jojoba oil esters of the present invention are a light yellow liquid with a slight, pleasant odor. The jojoba oil esters are essentially devoid of tars, resins, alkaloids, phosphatides, chlorophyll and other impurities. The jojoba oil esters may be bleached and or in grades that have been bleached and deodorized. Jojoba oil esters of the present invention have a high oxidative and thermal stability. In this aspect of the invention, the jojoba oil esters have an oxidative stability of at least about 68 hours at 110° C. and a thermal stability of at least about 295° C. The oxidative and thermal stabilities coupled with a lack of support for microbial growth provide a product with a shelf life of at least about two years.

Jojoba oil esters are from about 97.2 to about 99.1% pure and include long chain, linear cis-monounsaturated liquid aliphatic esters of the following fatty acids and fatty alcohols.

| Fatty Acids | % Range | % Preferred Range | % High Docosonal Range |
|---|---|---|---|
| 18:1 | 4–8 | 4.9–7.5 | 4.1–4.7 |
| 20:1 | 35–40 | 36.3–38.6 | 37.9–39.0 |
| 22:1 | 6–8.5 | 6.4–8.1 | 7.3–7.6 |
| 24:1 | 0.5–1.5 | 0.6–1.2 | 0.9–1.1 |

| Fatty Alcohols | % Range | % Preferred Range | % High Docosonal Range |
|---|---|---|---|
| 18:1 | 0.5–1 | 0.5–0.9 | 0.5 |
| 20:1 | 19–26.5 | 19.6–26.1 | 19.4–20.1 |
| 22:1 | 18–23.5 | 18.1–23.1 | 22.9–23.3 |
| 24:1 | 2–5 | 2.3–4.8 | 4.2–4.6 |

In an important aspect of the invention, the jojoba oil esters provide advantages in treating viral infections and skin disorders in that they deliver a high dose of rapidly absorbed active ingredient and that active ingredient may be of several different configurations. The esters and/or their metabolites have an array of differing chain lengths. The different chain lengths of the esters and their metabolites may have different rates and pathways for permeating the skin and moving into position between the parasitic virus and the plasma membrane of the host cell. They also have different efficacy when inhibiting the replication of different viruses. These differences become even more important when treating different skin locations of patients of different age, sex, ethnic background, viral dose, location of infection, viral mutations, viral virulence and host resistance, general health status and immune system status. In this aspect of the invention, not only aliphatic alcohols, but their acid metabolites may act as active agents as cells are known to extensively metabolize the internalized fatty alcohol.

Application of Jojoba Oil Esters

The jojoba oil esters of the present invention may be directly applied to the skin in the afflicted area. One drop of jojoba oil esters solution is applied to the afflicted area at the earliest warning prodromal sensation of tingling, burning or itching. This may be repeated after 15 minutes and 30 minutes. In most cases, this application prevents an outbreak, but if a blister forms, then application of jojoba oil ester is increased to one drop four times a day for one week or until redness is gone.

A typical application will include a virustatically effective amount of jojoba oil esters. As used herein, a "virustatically effective amount" of jojoba oil esters is about one to two drops of jojoba oil esters per about a 4 square centimeter area, and in a preferred aspect about one drop of jojoba oil ester per about a 4 square centimeter area. In this aspect of the invention, about 28 drops of jojoba oil ester has a weight of about 1 gram.

In an important aspect of the invention, the jojoba oil esters do not need to be mixed with emollients or surfactants. As used in the present application, "emollient free" or "surfactant free" refers to a composition having less than about 0.1 weight percent emollient or less than 0.1 weight percent surfactant, based on the weight of the final composition, preferably 0 weight percent emollient and 0 weight percent surfactant.

In another important aspect, patients may use the jojoba oil esters of the present invention prophylactically. Application of jojoba oil esters is effective for preventing inflamation, pain and visible signs of outbreaks of HSV when applied at prodrome stage. Patients also may apply jojoba oil esters prophylactically if they are known to have frequent outbreaks, during known times of outbreaks, such as pre-menstrually, and prior to occasions where outbreaks are particularly undesirable. The multiple mode of action provided by the jojoba oil esters of the present invention makes development of virus resistance less likely. In this aspect of the invention, about one to two drops of jojoba oil esters are applied directly to the skin where outbreaks usually occur. Application is about every 30 minutes for about three doses.

Production of Jojoba Oil Esters

Jojoba oil esters constitute about 50% of the weight of jojoba seeds that are annually harvested from jojoba trees grown in orchards in the Sorora Desert of Arizona, California and Mexico. During annual maturation of the seeds, long-chain cis monounsaturated aliphatic esters result from esterification of omega-9 monounsaturated linear fatty acids and omega-9 monounsaturated linear fatty alcohols utilizing enzymes including, four elongases, an acyl-CoA reductase and an acyl transferase that have been identified in the seeds. (Lassner, M. W. et al., Prodeedings, perspectives on new crops and new uses, 1999, Producing Wax Esters in Transgenic Plants by Expression of Genes Derived from Jojoba)

Golden jojoba oil is separated from the non-oil part of the seeds by crushing and filtration. Refined, bleached and deodorized jojoba oil can then be made from golden jojoba oil by standard methods well known in the industry. Organic certified jojoba oil is grown, processed, transported and stored utilizing prescribed methods required for organic certification, basically the plants, including the seeds and oil are not exposed to pesticides or synthetic chemicals. Hydrogenation is accomplished by reacting the refined, bleached, deodorized jojoba oil with hydrogen using a nickel catalyst with procedures well known in the industry. Partial or completely hydrogenated jojoba oil has a higher melting point and increased viscosity. Molecular distillation is done by short-path molecular distillation that uses different pressures, exposure times and temperatures to further purify the jojoba oil or to separate different fractions as with a higher percentage of longer chains or shorter chains, based on differences in boiling points. Interesterification reactions, for example between jojoba oil and fully hydrogenated jojoba using a sodium methylate catalyst, break the ester linkage between the aliphatic acids and aliphatic alcohols. With completion of the reaction there is a random regrouping of the acids and alcohols with formation of new bonds.

Viruses that can be treated with jojoba oil esters

Viruses that can be treated by jojoba oil esters include the enveloped viruses, particularly of the herpes family. The herpesviruses is a family of DNA viruses having a virion 150–200 nm in diameter consisting of four components: a lipid bilayer enveloped with surface projections, a tegument of amorphous material, an icosahedral nucleocapsid with 162 prismatic capsomers, and a protein spool on which the DNA is wrapped. The genome consists of a single molecule of linear double-stranded DNA (MW 70–150×106, size 120–200 kbp). Viruses contain at least 30 structural polypeptides and are sensitive to lipid solvents, heat, and extremes of pH. Replication occurs in the nucleus and the enveloped is acquired by budding through the inner lamella of the nuclear membrane; virions are released by transport via the endoplasmic reticulum to the cell membrane.

Persistence for the lifetime of the host is common and some herpesviruses induce neoplasia. There are three subfamilies of this virus that include *Alphaherpesvirinae, Betaherpesvirinae,* and *Gammaherpesvirinae*. A larger number of herpesviruses have not yet been assigned to a subfamily or genus. Herpes simplex virus-1 (HSV 1), also named herpes labialis, that causes facial irritation and lesions can also be treated with jojoba oil esters.

Other viruses that have been shown to be affected by long chain monounsaturated aliphatic alcohols and acids, such as are part of our jojoba oil esters include, but are not limited to Herpes simplex virus-2 (HSV 2); also named herpes genitalis, which causes genital area irritations and lesions, Herpes simplex virus-3 HSV 3, also named herpes zoster and Varicella zoster, which causes chicken pox and shingles, Human herpes virus-8 (HSV 8), which causes the skin cancer named Kaposi sarcoma, Human Immunodeficiency Virus (HIV) that causes AIDS, Herpes simplex virus that causes infectious mononucleosis, Cytomegalic inclusion virus, Epstein-Barr virus, and HSV causing keratitis (of the eye).

Formulations of Jojoba Oil Esters

In an alternative aspect of the invention, the jojoba oil esters of the present invention may be provided as a mixture with conventional excipients, i.e., pharmaceutically acceptable organic or inorganic carrier substances suitable for parenteral application which do not deleteriously react with the jojoba oil esters. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, and the like. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The jojoba oil esters of the present invention when mixed with other excipients as described above may be applied as a topical agent, either in nonsprayable or sprayable form. Non-sprayable forms can be semi-solid or solid forms comprising a carrier indigenous to topical application and having a dynamic viscosity preferably greater than that of water. Suitable formulations include, but are not limited to, solutions, suspensions, emulsions, creams, ointments, powders, liniments, salves and the like. If desired, these may be sterilized or mixed with auxiliary agents, e.g., preservatives, stabilizers, wetting agents, buffers or salts for influencing osmotic pressure and the like. Preferred vehicles for non-sprayable topical preparations include ointment bases, e.g., polyethylene glycol-1000 (PEG-1000); conventional ophthalmic vehicles; creams, e.g., HEB cream; and gels, e.g., K-Y gel; as well as petroleum jelly and the like. These topical preparations may also contain emollients, perfumes and/or pigments to enhance their acceptability for various usages.

Formulation of Active Ingredients with Jojoba Oil Esters

In another aspect of the invention various active ingredients may be blended with the jojoba oil esters of the present invention to enhance the effectiveness of those active ingredients. Any active ingredient that is compatible with the jojoba oil ester and which may have its effectiveness enhanced by blending with jojoba oil, or have its transdermal adsorption enhanced by jojoba oil esters may be utilized.

Active ingredients may be blended with jojoba oil esters at their recommended dosage rates and the mixture can then be applied to the skin as described herein. The jojoba oil esters are effective for enhancing percutaneous adsorption and hence, the efficacy of the active ingredient.

Formulation of Immunomodulators with Jojoba Oil Esters

In another aspect of the invention, the jojoba oil esters of the present invention are effective for enhancing immunomodulators. As used herein "immunomodulator" refers to an agent which is able to modulate, i.e., enhance or decrease, an immune response. Examples of such modulation include an enhancement of a T-cell response and antibody production.

Any immunomodulator that is compatible with the jojoba oil ester and which may have its effectiveness enhanced by blending with jojoba oil esters, or have its transdermal adsorption enhanced by jojoba oil esters may be utilized. In this aspect of the invention, jojoba oil esters may be mixed with immunomodulators, such as for example imiquimod, and applied as described herein. In an important aspect, about 5 weight percent imiquimod is mixed with the jojoba oil esters and applied to the skin. The term "antigen" as used herein refers to a molecule which is capable of immunoreactivity with an appropriate T cell antigen receptor.

The jojoba oil esters of the present invention may also be used as an adjuvant. In this aspect of the invention, jojoba oil esters are blended with an antigen and then administered by know methods to elicit and immune response to the antigen. Antigens may include proteins, peptides and short oligopeptides, including synthetically produced and short oligopeptides, and oligopeptide mimics (i.e., organic compounds which mimic the T cell antigen receptor-binding properties of authentic immunogenic peptides), and combinations thereof.

The following examples illustrate methods for carrying out the invention and should be understood to be illustrative of, but not limiting upon, the scope of the invention which is defined in the appended claims.

EXAMPLES

Example 1

Use of Jojoba Oil Esters to Treat Herpes Simplex

Protocol

The study included male and female subjects with a history of multiple Herpes simplex infections that were either HSV1 facial herpes or HSV2 genital herpes. There was non intentional discrimination as to age, sex, and educational or ethnic background.

In this study 57 subjects compared jojoba oil ester treatment with previously used remedies, including no treatment at all. Each subject was given directions as to how to apply the jojoba oil esters. Subjects were advised to begin treatment at the very earliest warning symptoms of burning, itching or tingling that precede a new cold sore outbreak. They were directed to apply one drop of the solution to the herpes area with their finger, then reapply it again in 15 minutes and at mealtimes and bedtime for three days.

The study utilized a survey sheet that included the average number of outbreaks per year in the past, time and date of this new outbreak and how many hours after the first symptoms before treatment was started. Subjects reported the number of doses applied, and the number of days from the onset until they were free of symptoms. They also rated the effectiveness of this treatment compared to previous remedies they had used.

Results

Results from survey of Herpes Simplex patients who treated themselves with Jojoba Oil esters were as follows. Of the 57 patients reported, 89.5% found jojoba oil esters to be more effective than their previous remedies.

| | | |
|---|---|---|
| Total number reporting: | 57 | |
| Average number of recurrences per year in the past: | 4.05 | outbreaks |
| Average number of hours after $1^{st}$ tingling until Rx began: | 4.58 | |
| Number of days from the onset to healed with jojoba oil esters? | | |
| Range reported | 1–9 | days |
| Average number of days reported: | 4.68 | days |
| Number who started within one hour of symptoms onset: | 14 | |
| Visible signs prevented when Rx began within 1 hour: | 9 | (64%) |
| Average number of applications of jojoba oil ester: | 7.96 | |

| | | |
|---|---|---|
| Jojoba was much more effective: | 40 | 70.2% |
| Jojoba was a little more effective: | 11 | 19.3% |
| Jojoba was average effectiveness: | 5 | 8.8% |
| Jojoba was a little less effective: | 1 | 1.8% |
| Jojoba was much less effective: | 0 | 0% |

Number who had used these medications (some used multiple remedies)

| Rx | Number of patients | JOE* much more effective | JOE a little More effective | JOE avg effective | JOE a little less effective | JOE much less effective | % reporting jojoba Ester more Effective |
|---|---|---|---|---|---|---|---|
| ABREVA | 10 | 6 | 2 | 2 | | | 80% |
| Acyclovir/Zovirax | 19 | 14 | 2 | 2 | 1 | | 84% |
| Lycine | 6 | 4 | | 2 | | | 67% |
| Viractin | 4 | 3 | | 1 | | | 75% |
| Herpecin-L | 4 | 3 | | 1 | | | 75% |
| Carmex | 5 | 5 | | | | | 100% |
| Camphopinique | 3 | 3 | | | | | 100% |
| Hydrogen peroxide | 2 | 1 | 1 | | | | 100% |
| Zilactin L | 2 | 2 | | | | | 100% |
| Lactinex | 2 | 2 | | | | | 100% |
| Herpacil | 1 | 1 | | | | | 100% |
| DMSO | 1 | | | 1 | | | 100% |
| Blistex | 2 | 1 | 1 | | | | 100% |
| Famavir | 1 | 1 | | | | | 100% |
| Aspirin | 1 | 1 | | | | | 100% |
| Avorax | 1 | | | 1 | | | 100% |

-continued

| Rx | Number of patients | JOE* much more effective | JOE a little More effective | JOE avg effective | JOE a little less effective | JOE much less effective | % reporting jojoba Ester more Effective |
|---|---|---|---|---|---|---|---|
| Denavir cream | 4 | | 2 | 1 | 1 | | 50% |
| Lysine cream | 3 | 3 | | | | | 100% |
| Valtrex | 2 | 1 | 1 | | | | 100% |
| Zithromax | 1 | 1 | | | | | 100% |
| Tobradex | 1 | 1 | | | | | 100% |

Number who had used these medications (some used multiple remedies)

*JOE is jojoba oil esters of the present invention

Example 2

Study of Percutaneous Absorption of Jojoba Oil Esters

This study measured percutaneous adsorption of jojoba oil esters by a modified method of surface recovery and surface disappearance (Bronaugh et al., Percutaneous Aborption, Drugs, Cosmetics, Mechanisms Methodology, 1999). The objective was to determine the non-evaporative reduction of jojoba oil esters from the surface of the skin as the jojoba oil esters are absorbed into the skin.

Protocol

Skin surface recovery was estimated by washing the study area of skin with water 15 minutes prior to application of one drop of jojoba oil esters to four areas (12:00, 3:00, 6:00 and 9:00 o'clock) of skin adjacent to the lips. Ten subjects were tested.

At each 20 minute time interval a different area was blotted with a 3M facial oil remover sheet, using firm pressure over the sheet for a 5 second period of time. The 12:00 o'clock area was blotted at 20 minutes, the 3:00 o'clock area was blotted at 40 minutes, etc.

The percentage of recovered jojoba oil esters on the 3M facial oil remover sheets at each 20 minute time interval was visually estimated by one examiner who compared these recoveries with a baseline "0 minute" recovery done with the same method the previous day.

Results

Recovered and absorbed jojoba oil esters from facial skin at 5 time intervals.

| Time (minutes) | % Recovered | % Absorbed |
|---|---|---|
| 0 | 100 | 0 |
| 20 | 50-70 | 30-50 |
| 40 | 30-50 | 50-70 |
| 60 | 10-15 | 85-90 |
| 80 | 0-5 | 95-100 |

Example 3

Evaporation of Jojoba Oil Esters From a Hard Surface

Protocol

The study compared disappearance by evaporation from a hard glass surfaces One drop of jojoba oil ester was applied to a hard gass surface. Evaporative loss was measured by observing the disappearance of jojoba oil esters from the surface.

Results

Jojoba oil applied to a hard surface did not observably evaporate for 15 to 20 days. Time for complete evaporation is more than eight weeks.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A method of treating or preventing infections from enveloped type viruses, the method comprising applying jojoba oil esters to the skin in an amount and for a time effective for inhibiting enveloped virus replication, wherein the jojoba oil esters are esters of fatty acids and fatty alcohols, the fatty acids that are esterified with the fatty alcohols include from 4% to 8% C18:1 fatty acid, from 35% to 40% C20:1 fatty acid, from 6% to 8.5% C22:1 fatty acid, and from 0.5% to 1.5% C24:1 fatty acid, and the fatty alcohols that are esterified with the fatty acids include from 0.5% to 1% C18:1 fatty alcohol, from 19% to 26.5% C20:1 fatty alcohol, from 18% to 23.5% C22:1 fatty alcohol, and from 2% to 5% C24:1 fatty alcohol.

2. A method of treating or preventing infections according to claim 1 wherein the jojoba oil esters are from about 97.2% to about 99.1% weight percent of the jojoba oil esters applied to the skin.

3. A method of treating or preventing infections according to claim 1 wherein the jojoba oil esters have a viscosity of about 33 cp to about 37 cp at 25° C.

4. A method of treating or preventing infections according to claim 1 wherein more than about 50% of the jojoba oil esters are absorbed into the skin in about 20 to about 40 minutes.

5. A method of treating or preventing infections according to claim 1 wherein the jojoba oil esters have an oxidative stability index of at least about 68 hours at 110° C. and a thermal stability of at least about 295° C.

6. A method of treating or preventing infections according to claim 1 wherein from about 97.2% to about 99.1% pure jojoba oil esters are applied to the skin.

7. A method of treating or preventing infections from herpes simplex virus, the method comprising applying jojoba oil esters to the skin in an amount and for a time effective for inhibiting replication of herpes simplex virus, wherein the jojoba oil esters are esters of fatty acids and fatty alcohols, the fatty acids that are esterified with the fatty alcohols include from 4% to 8% C18:1 fatty acid, from 35% to 40% C20:1 fatty acid, from 6% to 8.5% C22:1 fatty acid, and from 0.5% to 1.5% C24:1 fatty acid, and the fatty alcohols that are esterified with the fatty acids include from 0.5% to 1% C18:1 fatty alcohol, from 19% to 26.5% C20:1 fatty alcohol, from 18% to 23.5% C22:1 fatty alcohol, and from 2% to 5% C24:1 fatty alcohol.

8. A method of treating or preventing infections according to claim 7 wherein the jojoba oil esters are from about 97.2% to about 99.1 weight percent of the jojoba oil esters applied to the skin.

9. A method of treating or preventing infections according to claim 7 wherein the jojoba oil esters have a viscosity of about 33 cp to about 37 cp at 25° C.

10. A method of treating or preventing infections according to claim 7 wherein more than about 50% of the jojoba oil esters are absorbed into the skin in about 20 to about 40 minutes.

11. A method of treating or preventing infections according to claim 7 wherein the jojoba oil esters have an oxidative stability index of at least about 68 hours at 110° C. and a thermal stability of at least about 295° C.

12. A method of treating or preventing infections according to claim 7 wherein from about one to about two jojoba oil esters are applied to the skin for each dosage.

13. A method of treating or preventing infections from herpes simplex virus, the method comprising applying jojoba oil esters to the skin in an amount and for a time effective for inhibiting replication of herpes simplex virus,
   wherein the jojoba oil esters are esters of fatty acids and fatty alcohols,
   wherein the fatty acids that are esterified with the fatty alcohols include from about 4% to about 8% C18:1 fatty acid, from about 35% to about 40% C20:1 fatty acid, from about 6% to about 8.5% C22:1 fatty acid, and from about 0.05% to about 1.5% C24:1 fatty acid,
   wherein the fatty alcohols that are esterified with the fatty acids include from about 0.5% to about 1% C18:1 fatty alcohol, from about 19% to about 26.5% C20:1 fatty alcohol, from about 18% to about 23.5% C22:1 fatty alcohol, and from about 2% to about 5% C24:1 fatty alcohol.

14. A method of treating or preventing infections according to claim 13 wherein the jojoba oil esters are from about 97.2 to about 99.1 weight percent of the jojoba oil esters applied to the skin.

15. A method of treating or preventing infections according to claim 13 wherein the jojoba oil esters have a viscosity of about 33 cp to about 37 cp at 25° C.

16. A method of treating or preventing infections according to claim 13 wherein more than about 50% of the jojoba oil esters are absorbed into the skin in about 20 to about 40 minutes.

17. A method of treating or preventing infections according to claim 13 wherein the jojoba oil esters have an oxidative stability index of at least about 68 hours at 110° C. and a thermal stability of at least about 295° C.

18. A method of treating or preventing infections according to claim 13 wherein from about one to two jojoba oil esters are applied to the skin for each dosage.

19. A method for enhancing effectiveness of active ingredients, the method comprising:
   mixing an active ingredient with jojoba oil esters,
   applying the active ingredient jojoba oil ester to skin in an amount effective for enhancing the effectiveness of the active ingredient,
   wherein the jojoba oil esters are esters of fatty acids and fatty alcohols, the fatty acids that are esterified with the fatty alcohols include from 4% to 8% C18:1 fatty acid, from 35% to 40% C20:1 fatty acid, from 6% to 8.5% C22:1 fatty acid, and from 0.5% to 1.5% C24:1 fatty acid, and the fatty alcohols that are esterified with the fatty acids include from 0.5% to 1% C18:1 fatty alcohol, from 19% to 26.5% C20:1 fatty alcohol, from 18% to 23.5% C22:1 fatty alcohol, and from 2% to 5% C24:1 fatty alcohol.

20. A method for enhancing effectiveness of active ingredients according to claim 19 wherein the active ingredient is selected from the group consisting of immune response modulators, anti-inflammatory drugs, antifungal agents, lipophilic vitamins, anti-neoplastic agents, hormonal agents, hair growth stimulators and anti-viral agents.

21. A method for modulating an immune response, the method comprising:
   mixing an immunomodulator with jojoba oil esters,
   applying the immunomodulator jojoba oil ester to skin in an amount effective for enhancing the effectiveness of the immunomodulator,
   wherein the jojoba oil esters are esters of fatty acids and fatty alcohols, the fatty acids that are esterified with the fatty alcohols include from 4% to 8% C18:1 fatty acid, from 35% to 40% C20:1 fatty acid, from 6% to 8.5% C22:1 fatty acid, and from 0.5% to 1.5% C24:1 fatty acid, and the fatty alcohols that are esterified with the fatty acids include from 0.5% to 1% C18:1 fatty alcohol, from 19% to 26.5% C20:1 fatty alcohol, from 18% to 23.5% C22:1 fatty alcohol, and from 2% to 5% C24:1 fatty alcohol.

* * * * *

UNITED STATES PATENT AND TRADEMARK OFFICE
CERTIFICATE OF CORRECTION

PATENT NO. : 6,559,182 B1
DATED : May 6, 2003
INVENTOR(S) : Hal Purcell

It is certified that error appears in the above-identified patent and that said Letters Patent is hereby corrected as shown below:

Column 15,
Line 17, after "two" insert -- drops of --.

Column 16,
Line 6, after "two" insert -- drops of --.

Signed and Sealed this

Third Day of June, 2003

JAMES E. ROGAN
*Director of the United States Patent and Trademark Office*